United States Patent
Tabor et al.

(10) Patent No.: US 10,273,332 B2
(45) Date of Patent: Apr. 30, 2019

(54) RECYCLE-CONTENT POLYESTER POLYOLS

(71) Applicant: Resinate Materials Group, Inc., Plymouth, MI (US)

(72) Inventors: Rick Tabor, Plymouth, MI (US); Eric D. Vrabel, Ferndale, MI (US); Kevin Anthony Rogers, Farmington, MI (US); Shakti L. Mukerjee, Canton, MI (US); Matthew J. Beatty, Ann Arbor, MI (US); Adam William Emerson, Ypsilanti, MI (US); Matthew T. Brown, Novi, MI (US); Jack Rogers Kovsky, Detroit, MI (US); Michael D. Kellerman, Ann Arbor, MI (US); Michael Robert Christy, Howell, MI (US)

(73) Assignee: RESINATE MATERIALS GROUP, INC., Plymouth, MI (US)

( * ) Notice: Subject to any disclaimer, the term of this patent is extended or adjusted under 35 U.S.C. 154(b) by 205 days.

(21) Appl. No.: 15/306,774

(22) PCT Filed: Apr. 30, 2015

(86) PCT No.: PCT/US2015/028642
§ 371 (c)(1),
(2) Date: Oct. 26, 2016

(87) PCT Pub. No.: WO2015/171432
PCT Pub. Date: Nov. 12, 2015

(65) Prior Publication Data
US 2017/0051103 A1    Feb. 23, 2017

Related U.S. Application Data

(60) Provisional application No. 61/988,855, filed on May 5, 2014.

(51) Int. Cl.
| | | |
|---|---|---|
| *C07C 67/03* | (2006.01) | |
| *C07C 69/82* | (2006.01) | |
| *C08G 18/42* | (2006.01) | |
| *C08G 18/72* | (2006.01) | |
| *C08G 63/87* | (2006.01) | |
| *C08J 11/24* | (2006.01) | |
| *C08G 63/183* | (2006.01) | |
| *C08G 63/553* | (2006.01) | |

(52) U.S. Cl.
CPC .............. *C08G 63/87* (2013.01); *C07C 67/03* (2013.01); *C08G 18/42* (2013.01); *C08G 18/4213* (2013.01); *C08G 18/72* (2013.01); *C08G 63/183* (2013.01); *C08G 63/553* (2013.01); *C08J 11/24* (2013.01); *Y02P 20/582* (2015.11)

(58) Field of Classification Search
CPC ......... C07C 67/03; C07C 69/82; C08G 63/87; C08G 63/183; C08G 18/72; C08G 18/4213; C08G 63/553; C08G 18/42; C08J 11/24; Y02P 20/582

See application file for complete search history.

(56) References Cited

U.S. PATENT DOCUMENTS

| | | | |
|---|---|---|---|
| 2,793,220 A | 5/1957 | Barrett et al. | |
| 4,371,469 A | 2/1983 | Foglia et al. | |
| 5,138,027 A | 8/1992 | Van Beek | |
| 5,502,247 A | 3/1996 | Bartos et al. | |
| 5,504,121 A | 4/1996 | West | |
| 5,602,187 A | 2/1997 | West | |
| 5,877,255 A * | 3/1999 | Gerber | C08G 18/4288 524/590 |
| 6,281,373 B1 | 8/2001 | Sato et al. | |
| 6,630,601 B1 | 10/2003 | Inada et al. | |
| 6,642,350 B1 | 11/2003 | Asakawa et al. | |
| 7,192,988 B2 | 3/2007 | Smith et al. | |
| 2012/0149791 A1 | 6/2012 | Felice et al. | |
| 2013/0261222 A1* | 10/2013 | Schiraldi | C09D 167/02 523/172 |

FOREIGN PATENT DOCUMENTS

| | | |
|---|---|---|
| CA | 104511 A | 4/1907 |
| EP | 1120394 A1 | 8/2001 |
| WO | 2000/075252 A1 | 12/2000 |

OTHER PUBLICATIONS

Paszun et al., Chemical Recycling of Poly(ethylene terephthalate), Ind. Eng. Chem. Res. 1997, 36, pp. 1373-1381.
Vaidya et al., J. Appl. Polym. Sci. 34 (1987) 235.
Saravari et al., J. Appl. Polym. Sci. 92 (2004) 3040.
Saravari et al., J. Appl. Polym. Sci. 105 (2007) 1802.

(Continued)

*Primary Examiner* — Rabon A Sergent
(74) *Attorney, Agent, or Firm* — Dilworth IP, LLC

(57) ABSTRACT

Polyester polyols made from recycled polyethylene terephthalate (rPET) and processes for making them are disclosed. The rPET is heated with a $C_3$-$C_{10}$ glycol reactant to give a digested intermediate comprising glycols and a terephthalate component, which comprises 45 to 70 wt. % of bis(hydroxyalkyl)terephthalates, and preferably lesser amounts of terephthalate dimers and trimers. Treatment of the digested intermediate with activated carbon gives a polyester polyol having a color index less than 20. The polyols have desirable hydroxyl numbers, viscosities, appearance, and other attributes for formulating polyurethane products and are a sustainable alternative to bio- or petrochemical-based polyols.

21 Claims, No Drawings

(56) References Cited

OTHER PUBLICATIONS

Ikladious, N., J. Elast. Plast. 32 (2000) 140.
Troev, K. et al., J. Appl. Polym. Sci. 90 (2003) 1148.
PCT International Search Report dated Jul. 14, 2015 from corresponding Application No. PCT/US2015/028642.

* cited by examiner

RECYCLE-CONTENT POLYESTER POLYOLS

FIELD OF THE INVENTION

The invention relates to polyol compositions produced from recycled polyethylene terephthalate. The polyols are useful for formulating polyurethanes and other condensation polymers.

BACKGROUND OF THE INVENTION

Aromatic polyester polyols are commonly used intermediates for the manufacture of polyurethane products, including flexible and rigid foams, polyisocyanurate foams, coatings, sealants, adhesives, and elastomers. The aromatic content of these polyols contributes to strength, stiffness, and thermal stability of the urethane product.

Commonly, the aromatic polyester polyol is made by condensing aromatic diacids, diesters, or anhydrides (e.g., terephthalic acid, dimethyl terephthalate) with glycols such as ethylene glycol, propylene glycol, diethylene glycol, or the like. These starting materials usually derive exclusively from petrochemical sources.

As companies increasingly seek to offer products with improved sustainability, the availability of intermediates produced from bio-renewable and/or recycled materials becomes more leveraging. However, there remains a need for these products to deliver equal or better performance than their traditional petroleum-based alternatives at a comparable price point.

Bio-renewable content alone can be misleading as an indicator of "green" chemistry. For example, when a food source such as corn is needed to provide the bio-renewable content, there are clear trade-offs between feeding people and providing them with performance-based chemical products. Additionally, the chemical or biochemical transformations needed to convert sugars or other bio-friendly feeds to useful chemical intermediates such as polyols can consume more natural resources and energy and can release more greenhouse gases and pollutants into the environment than their petro-based alternatives in the effort to achieve "green" status.

Waste thermoplastic polyesters, including waste polyethylene terephthalate (PET) streams (e.g., from plastic beverage containers), provide an abundant source of raw material for making new polymers. Usually, when PET is recycled, it is used to make new PET beverage bottles, PET fiber, or it is chemically transformed to produce polybutylene terephthalate (PBT). Other recycled raw materials are also available. For example, recycled propylene glycol is available from aircraft or RV deicing and other operations.

Urethane formulators demand polyols that meet required specifications for color, clarity, hydroxyl number, functionality, acid number, viscosity, particulates, and other properties. These specifications will vary and depend on the type of urethane application. For instance, rigid foams generally require polyols with higher hydroxyl number than the polyols used to make flexible foams.

Polyols suitable for use in making urethanes have proven difficult to manufacture from recycled materials, including recycled polyethylene terephthalate (rPET). Many references describe digestion of rPET with glycols (also called "glycolysis"), usually in the presence of a catalyst such as zinc or titanium. Digestion converts the polymer to a mixture of glycols and low-molecular-weight PET oligomers. Although such mixtures have desirably low viscosities, they often have high hydroxyl numbers or high levels of free glycols. Frequently, the target product is a purified bis (hydroxyalkyl) terephthalate (see, e.g., U.S. Pat. Nos. 6,630, 601, 6,642,350, and 7,192,988) or terephthalic acid (see, e.g., U.S. Pat. No. 5,502,247). Some of the efforts to use glycolysis product mixtures for urethane manufacture are described in a review article by D. Paszun and T. Spychaj (*Ind. Eng. Chem. Res.* 36 (1997) 1373.

Most frequently, ethylene glycol is used as the glycol reactant for glycolysis. This is sensible because it minimizes the possible reaction products. Usually, the glycolysis is performed under conditions effective to generate bis(hydroxyethyl) terephthalate ("BHET"), although sometimes the goal is to recover pure terephthalic acid. When ethylene glycol is used as a reactant, the glycolysis product is typically a crystalline or waxy solid at room temperature. Such materials are less than ideal for use as polyol intermediates because they must be processed at elevated temperatures. Polyols are desirably free-flowing liquids at or close to room temperature.

Gel permeation chromatography has been used to identify components of mixtures produced by glycolysis of rPET, although the reported results are not necessarily in agreement about the proportion of terephthalate monomer, dimer, and trimer products generated. For instance, Vaidya et al. (*J. Appl. Polym. Sci.* 34 (1987) 235) teach that depolymerization of PET waste using 37.5, 50, or 62.5 wt. % of propylene glycol and zinc acetate catalyst (200° C., 8 h) provides a mixture in which the major fractions are identified as monomeric, i.e., species that have a single terephthalate unit (BHET, bis(hydroxypropyl) terephthalate ("BHPT"), and the mixed bis(hydroxyalkyl) terephthalate monomer). In two papers (*J. Appl. Polym. Sci.* 92 (2004) 3040; 105 (2007) 1802), Saravari et al. describe the synthesis of urethane oils from palm oil and waste PET bottles. In an initial step, the PET is depolymerized using propylene glycol (62.5 wt. %) and zinc acetate (190° C., 6 h). The GPC chromatogram of the glycolized product from the 2004 paper (FIG. 1, p. 3042) shows what appears to be a mixture of dimer (458 mol. wt.) and trimer (844 mol. wt.), although the text suggests that monomers are also present. A similar chromatogram in the 2007 paper (FIG. 2, p. 1804) reveals what appears to be roughly a 1:3:1 mixture of monomer (249 mol. wt.), dimer (553 mol. wt.), and trimer (831 mol. wt.), prepared by the same method used earlier, and the text is consistent with this interpretation. Further, Ikladious (*J. Elast. Plast.* 32 (2000) 140) describes waste PET depolymerization with propylene glycol (40-60 wt. %) and zinc acetate (200° C., 10 h). GPC chromatograms (FIGS. 1-3) indicate two predominant products (473 and 759 mol. wt.), which the authors attribute to dimer and trimer products, respectively. Using more propylene glycol tilts the product mixture in the direction of more dimer. Interestingly, however, despite similar process conditions compared with those used by the other authors, the GPC trace shows no monomers.

Because rPET is frequently colored with dyes (e.g., green PET used for soda bottles), activated carbon treatment has been used to reduce the color level during the preparation of BHET or terephthalic acid. For instance, U.S. Pat. No. 7,192,988 teaches a two-stage process for color removal. Recycled PET is depolymerized to give BHET, which is treated with activated carbon to remove some color. The remaining dye is removed by extraction with water, alcohol, or glycol to recover purified BHET, which can be used as a monomer for making PET. For additional examples of activated carbon treatment, see U.S. Pat. Nos. 5,504,121; 5,602,187; 6,630,601; and 6,642,350. Extraction methods have also been used to remove color from glycolized, colored rPET (see, e.g., U.S. Publ. No. 2012/0149791). Thus, there has been limited activity in converting rPET to useful polyol compositions and even less interest in removing color from such compositions, as prior color removal efforts tend to focus on purified monomer compositions.

Improved polyols are needed. In particular, the urethane industry needs sustainable polyols based in substantial part on recycled polymers such as the practically unlimited supply of recycled polyethylene terephthalate. Polyols with high recycle content that satisfy the demanding color, clarity, viscosity, functionality, and hydroxyl content requirements of polyurethane formulators would be valuable.

SUMMARY OF THE INVENTION

The invention relates to a polyester polyol and process for making it. The polyol is made by a process which comprises two steps. First, a composition comprising recycled polyethylene terephthalate ("rPET") is heated with a $C_3$-$C_{10}$ glycol reactant to give a digested intermediate comprising glycols and a terephthalate component. The molar ratio of glycol reactant to rPET is at least 2.0. The terephthalate component comprises, by gel permeation chromatography, 45 to 70 wt. % of bis(hydroxyalkyl)-terephthalates. In a second step, the digested intermediate is treated with activated carbon under conditions effective to give the polyester polyol. The resulting polyol has a hydroxyl number within the range of 25 to 800 mg KOH/g and a color index less than 20. The polyols, which are valuable for formulating polyurethane dispersions, flexible and rigid foams, coatings, adhesives, sealants, and elastomers, provide a sustainable alternative to bio- or petrochemical-based polyols.

DETAILED DESCRIPTION OF THE INVENTION

Recycled polyethylene terephthalate suitable for use in making the inventive polyester polyols can come from a variety of sources. The most common source is the post-consumer waste stream of PET from plastic bottles or other containers. The rPET can be colorless or contain dyes (e.g., green, blue, or other colors) or be mixtures of these. In a preferred aspect, the rPET is green only, green rPET plus colorless rPET, green rPET plus rPET containing other dyes, or some other combination that includes green rPET. A minor proportion of organic or inorganic foreign matter (e.g., paper, other plastics, glass, metal) can be present. A desirable source of rPET is "flake" rPET, from which many of the common impurities present in scrap PET bottles have been removed in advance. Another desirable source of rPET is pelletized rPET, which is made by melting and extruding rPET through metal filtration mesh to further remove particulate impurities. Because PET plastic bottles are currently manufactured in much greater quantity than any recycling efforts can match, scrap PET will continue to be available in abundance.

The rPET is heated with a $C_3$-$C_{10}$ glycol reactant. Suitable glycol reactants are well known. By "glycol," we mean a linear or branched, aliphatic or cycloaliphatic compound or mixture of compounds having two or more hydroxyl groups. Other functionalities, particularly ether or ester groups, may be present in the glycol. In preferred $C_3$-$C_{10}$ glycol reactants, two of the hydroxyl groups are separated by from 2 to 10 carbons, preferably 2 to 6 carbons. Suitable glycols include, for example, propylene glycol, 1,3-propanediol, 1,2-butylene glycol, 1,3-butylene glycol, 1,4-butanediol, 2-methyl-1,3-propanediol, neopentyl glycol, glycerol, trimethylolpropane, 3-methyl-1,5-pentanediol, 1,4-cyclohexanedimethanol, diethylene glycol, dipropylene glycol, triethylene glycol, tripropylene glycol, 1,6-hexanediol, and the like, and mixtures thereof. Preferably, the $C_3$-$C_{10}$ glycol reactant is selected from propylene glycol, diethylene glycol, 1,4-butanediol, triethylene glycol, dipropylene glycol, neopentyl glycol, 2-methyl-1,3-propanediol, 3-methyl-1,5-pentanediol, 1,6-hexanediol, and mixtures thereof. Propylene glycol is particularly preferred. In a preferred aspect, the glycol is a recycled glycol, especially recycled propylene glycol. Propylene glycol recovered from used deicing fluids is one example.

The rPET and $C_3$-$C_{10}$ glycol reactant are heated, optionally in the presence of a catalyst, to give a digested intermediate comprising glycols and a terephthalate component. The glycols will include $C_3$-$C_{10}$ glycol reactant and ethylene glycol generated from glycolysis of the rPET. The terephthalate component comprises, by gel permeation chromatography using ultraviolet detection, 45 to 70 wt. % of bis(hydroxyalkyl)terephthalates, also referred to herein as "monomer." In one aspect, the terephthalate component further comprises 20 to 40 wt. % of terephthalate dimers. In a further preferred aspect, the terephthalate component of the digested intermediate comprises 45 to 65 wt. % of bis(hydroxyalkyl)terephthalates, 20 to 35 wt. % of terephthalate dimers, and 5 to 15 wt. % of terephthalate trimers. In another preferred aspect, the terephthalate component comprises 50 to 60 wt. % of bis(hydroxyalkyl)-terephthalates, 25 to 30 wt. % of terephthalate dimers, and 8 to 12 wt. % of terephthalate trimers. Heating is advantageously performed at temperatures within the range of 80° C. to 260° C., preferably 100° C. to 240° C., more preferably 130° C. to 210° C., and most preferably 160° C. to 185° C.

Catalysts suitable for making the digested intermediate are well known (see, e.g., K. Troev et al., *J. Appl. Polym. Sci.* 90 (2003) 1148). In particular, suitable catalysts comprise titanium, zinc, antimony, germanium, zirconium, manganese, or other metals. Specific examples include titanium alkoxides (e.g., tetrabutyl titanate), titanium(IV) phosphate, zirconium alkoxides, zinc acetate, lead acetate, cobalt acetate, manganese(II) acetate, antimony trioxide, germanium oxide, or the like, and mixtures thereof. Catalysts that do not significantly promote isocyanate reaction chemistries are preferred. The amount of catalyst used is typically in the range of 0.005 to 5 wt. %, preferably 0.01 to 1 wt. %, more preferably 0.02 to 0.7 wt. %, based on the total amount of polyol being prepared.

Usually, the digestion reaction is performed by heating the rPET, $C_3$-$C_{10}$ glycol reactant, and any catalyst at least until the mixture completely liquefies and particles of the rPET are no longer apparent. Reaction times range from about 30 minutes to about 16 hours, more typically 1 to 10 hours, preferably 2 to 8 hours, and will depend on the reaction temperature, source of the rPET, the particular glycol reactant used, mixing rate, desired degree of depolymerization, equipment limitations, reaction scale, and other factors that are within the skilled person's discretion.

The molar ratio of $C_3$-$C_{10}$ glycol reactant to rPET is at least 2.0, preferably 2.0 to 6.0, more preferably 2.5 to 4.5. When the glycol/rPET molar ratio is below 2.0, the products are often solids or too viscous to be practical for use as polyols. On the other hand, when the glycol/rPET molar ratio is greater than about 6, the hydroxyl numbers tend to exceed the practical upper limit of about 800 mg KOH/g.

The digested intermediate is treated with activated carbon under conditions effective to give a polyester polyol having a color index less than 20, preferably less than 15. Color index is defined by 100×(|a*|/L*) as measured by CIE colorimetric analysis. When the rPET includes green rPET, the a* value will often be a high negative value. The carbon-treated polyol will have a higher value, usually a low negative value. For instance, a green rPET might have an a* value of −45, while a carbon-treated polyol might have an a* value of −10. The absolute value of a* (i.e., |a*|) is used to compute the color index using the above formula. Any suitable means can be used to perform the colorimetric analysis via transmission through the liquid polyol. It is convenient to measure transmission spectral properties using a spectrophotometer such as a Cary® 100 Conc UV/vis spectrophotometer (Varian), an X-Rite color 8200 spectrophotometer, an X-Rite color i7 spectrophotometer, or similar equipment.

Activated carbon comes in many suitable forms, and the form actually used will depend on reactor design, process scale, the nature of the digested intermediate to be treated, and other factors. The activated carbon is normally produced from carbonaceous sources such as nutshells, coconut husks, peat, wood, coal, or other sources. Raw material is typically activated and/or carbonized chemically by treatment with acids, bases, or salts at temperatures up to about 900° C. Thereafter, it may be carbonized and/or oxidized by heating either in the presence or absence of an oxygen-containing gas (e.g., air or steam) at 600° C. or higher. A combination of treatments can be used. Suitable activated carbons are supplied as powders, granules, beads, extrudates, or other forms. Preferably, the activated carbon has a surface area greater than 300 m$^2$/g, more preferably greater than 500 m$^2$/g. A preferred range for the surface area is 500 m$^2$/g to 2000 m$^2$/g. Suppliers include, for example, Paro Chemical, Jacobi Carbons, Calgon Carbon, Norit Americas, and many others.

The amount of activated carbon needed will depend on the source of the rPET, the treatment unit design, temperature, the degree of color reduction needed, and other factors. Preferably, the activated carbon is used in an amount within the range of 0.1 to 10 wt. %, more preferably 0.5 to 5 wt. %, based on the amount of digested intermediate to be treated.

The carbon treatment is preferably performed by combining a warm or hot (30° C. to 180° C., preferably 45° C. to 150° C., most preferably 50° C. to 120° C.) digested intermediate with the activated carbon, mixing until homogeneous, and allowing the carbon and digested intermediate to remain in contact for several minutes to several hours, preferably from 10 minutes to 4 hours. It is convenient to simply stir the carbon-treated intermediate at the desired temperature for the duration of the treatment.

Following treatment with activated carbon, the digested intermediate is preferably filtered using a filter aid such as diatomaceous earth (e.g., Celite® 545), molecular sieves, clays, inorganic oxides (aluminas, silicas, silica-aluminas, magnesium silicates, etc.), or the like. Diatomaceous earth is particularly preferred. Filtration, especially when using a filter aid, removes the activated carbon, impurities adsorbed by the activated carbon, undigested PET particles, and other insoluble material including residual plastics, metal, paper, or other impurities. Heat, pressure, recirculation through the filtration medium to effectively produce multiple filtrations, or some combination of these may be used to reduce filtration time or improve results. It may be desirable, for instance, to pre-heat the filter and/or polyol before use and to perform the filtration in the presence of heat to reduce viscosity and enhance process efficiency. The examples below demonstrate one way to accomplish this. Additionally, it may be desirable to perform multiple filtrations to obtain a more highly purified polyester polyol.

The inventive polyester polyols have hydroxyl numbers within the range of 25 to 800 mg KOH/g, preferably 40 to 500 mg KOH/g, more preferably 200 to 400 mg KOH/g. Hydroxyl number can be measured by any accepted method for such a determination, including, e.g., ASTM E-222 ("Standard Test Methods for Hydroxyl Groups Using Acetic Anhydride Acetylation").

The inventive polyols are flowable liquids under ambient conditions, which is a distinct advantage for formulating polyurethanes when compared with intermediates that must be melted prior to use. Preferably, the polyols have viscosities measured at 25° C. less than 30,000 cP, more preferably less than 20,000 cP, most preferably less than 10,000 cP. A preferred range for the polyol viscosity is 100 to 9,000 cP, more preferably 300 to 3,900 cP. Viscosity can be determined by any industry-accepted method. It is convenient to use, for instance, a Brookfield viscometer (such as a Brookfield DV-III Ultra rheometer) fitted with an appropriate spindle, and to measure a sample at several different torque settings to ensure an adequate confidence level in the measurements.

The polyols preferably have low acid numbers. Urethane manufacturers will often require that a polyol have an acid number below a particular specification. Low acid numbers can be ensured by using an adequate excess of $C_3$-$C_{10}$ glycol reactant, driving the glycolysis and/or hydrophobe condensation steps to the desired level of completion, or by adding a neutralizing agent (e.g., sodium hydroxide). Preferably, the polyols have an acid number less than 30 mg KOH/g, more preferably less than 10 mg KOH/g, and most preferably less than 5 mg KOH/g. As suggested above, it is acceptable practice to adjust acid numbers if necessary for a particular application with an acid scavenger such as, for example, an epoxide derivative, and this treatment can be performed by the manufacturer, distributor, or end user.

In certain aspects, the inventive polyester polyols may be modified with a hydrophobe. The timing for introducing the hydrophobe can vary. In one preferred aspect, the hydrophobe is included with the $C_3$-$C_{10}$ glycol reactant and rPET in the digestion process. In another preferred example, the hydrophobe is condensed with the digested intermediate prior to activated carbon treatment. Example 6 below illustrates this approach. If desired, the hydrophobe can also be reacted with the polyol after activated carbon treatment (for instance, see Example 7, below).

Suitable hydrophobes are relatively nonpolar, carbon-rich compositions. Classes of hydrophobes suitable for use in modifying the polyester polyols include, for example, vegetable oils (soybean oil, castor oil, linseed oil, tung oil, corn oil, canola oil, or the like), fatty acids (lauric, stearic, oleic, myristic, palmitic, linoleic, or linolenic acids, or the like), alkyl esters of fatty acids, fatty esters of fatty acids, fatty alcohols, Guerbet alcohols, dimer fatty acids, dimer fatty alcohols, trimer fatty acids, trimer fatty alcohols, $C_{10}$-$C_{36}$ branched alcohols, $C_{10}$-$C_{36}$ alkoxylated alkylphenols (e.g., alkoxylated nonylphenol or alkoxylated cardanol), and diol or polyol derivatives of these hydrophobes.

Dimer fatty acids are particularly preferred hydrophobes. As used herein, "dimer fatty acid" is synonymous with "dimerized fatty acid" or "dimer acid." Dimer fatty acids are chemical intermediates made by dimerizing unsaturated fatty acids (e.g., oleic acid, linoleic acid, linolenic acid, ricinoleic acid) in the presence of a catalyst, such as a bentonite or montmorillonite clay. Commercially available dimer fatty acids are usually mixtures of products in which the dimerized product predominates. Some commercial dimer acids are made by dimerizing tall oil fatty acids. Dimer fatty acids frequently have 36 carbons and two carboxylic acid groups. They may be saturated or unsaturated. They may also be hydrogenated to remove unsaturation. In a preferred aspect, the dimer fatty acid comprises dimerized oleic acid, trimerized oleic acid, dimerized linoleic acid, trimerized linolelic acid, dimerized linolenic acid, trimerized linolenic acid, or mixtures thereof. Suitable dimer fatty acids include Pripol™ dimer fatty acids (products of Croda) such as Pripol™ 1006, 1009, 1010, 1012, 1013, 1017, 1022, 1025, 1027, 1029, 1036, and 1098; Unidyme™ dimer acids (products of Arizona Chemical) such as Unidyme 10, 14, 18, 22, 35, M15, and M35; dimer acids available from Emery Oleochemicals, and FloraDyme™ dimer acids from Florachem Corporation.

Methods for synthesizing dimer fatty acids suitable for use are also known. Fatty acids having at least one carbon-carbon double bond are dimerized in the presence of a catalyst such as a montmorillonite, kaolinite, hectorite, or attapulgite clay (see, e.g., U.S. Pat. Nos. 2,793,220, 4,371,469, 5,138,027, and 6,281,373, the teachings of which are incorporated herein by reference; see also WO 2000/075252 and CA 104511).

When a hydrophobe is included, it is introduced under conditions effective to promote condensation between one or more functional groups of the hydrophobe (e.g., acid groups of a dimer fatty acid) and hydroxyl groups present (or to be generated) in the digested intermediate. The condensation is preferably performed by heating at temperatures within the range of 80° C. to 260° C., preferably 100° C. to 240° C., more preferably 130° C. to 230° C., and most preferably 160° C. to 210° C. Water generated in this reaction is advantageously removed from the reaction mixture as it forms. On a lab scale, it is convenient to use a Dean-Stark trap or similar apparatus to remove the water of reaction, but other means will be more practical on a larger scale. Continuous processes for water removal, such as vacuum stripping, sparging the reaction mixture with dry inert gases, wiped-film evaporation, and the like, may be desirable. The condensation reaction is normally continued until a predetermined amount of water has been collected or a target acid number and/or hydroxyl number is reached for the product.

When a hydrophobe is used, the molar ratio of hydrophobe to rPET can vary depending on the nature of the hydrophobe, the desired attributes of the polyester polyol, the reaction conditions, and other factors. Preferably, 0.2 to 2 moles, more preferably 0.3 to 1 mole, of the hydrophobe is used per mole of rPET repeat unit. When the molar ratio is less than 0.2, there is too little benefit from including the hydrophobe. When the molar ratio is greater than 2, formulation cost is higher than desirable, recycle content drops, and there is little or no additional performance benefit.

An advantage of the polyester polyols is their reduced reliance on bio- or petrochemical sources for raw material. Preferably, the polyols include greater than 10 wt. %, more preferably greater than 25 wt. %, most preferably greater than 50 wt. % of recycle content. A preferred range for the recycle content is 25 to 98.5 wt. %. By "recycle content," we mean the combined amounts of rPET and any recycled $C_3$-$C_{10}$ glycol reactant. Some glycols, such as propylene glycol, are available as recovered or recycled materials. For instance, propylene glycol is used in deicing fluids, and after use, it can be recovered, purified, and reused. Recycle content can be calculated, for instance, by combining the masses of rPET and any recycled glycol reactant, dividing this sum by the total mass of reactants (glycol reactants, rPET, and any hydrophobe), and then multiplying the result by 100.

The polyols can be reacted with polyisocyanates to generate polyurethanes, polyisocyanurates, or prepolymers and can be used to formulate a wide variety of polyurethane products. Hydrophobicity can be adjusted if desired by judicious selection of the hydrophobe. The ability to control hydrophobicity is particularly valuable in the coatings industry. The polyols can be used for cellular, microcellular, and non-cellular applications including flexible foams, rigid foams (including polyisocyanurate foams), urethane dispersions, coatings, adhesives, sealants, elastomers, and radiation-curable (meth)acrylate derivatives. The resulting polyurethanes and derivatives are potentially useful for automotive and transportation applications, building and construction products, marine products, packaging foam, flexible slabstock foam, carpet backing, appliance insulation, cast elastomers and moldings, footwear, biomedical devices, and other applications.

The following examples merely illustrate the invention; the skilled person will recognize many variations that are within the spirit of the invention and scope of the claims.

Examples 1-5

Preparation and Carbon Treatment of Glycol-Digested Polyol from Recycled PET

A reactor equipped with an overhead mixer, condenser, heating mantle, thermocouple, and nitrogen inlet is charged with zinc acetate dihydrate (0.55 wt. %), green recycled polyethylene terephthalate pellets, and a glycol reactant (see Table 1 for reactant and molar amount per mole of rPET). The mixture is heated without stirring to about 130° C. Stirring is then commenced at 60 rpm, and heating continues until the reactor contents reach 180° C. The mixture is heated until no particles of rPET remain (about 4 h). When the digestion reaction is considered complete, the mixture is cooled to about 100° C. and is then decanted from the reactor and filtered through cheesecloth. A first portion of the product is analyzed without further treatment. A second portion of the product is treated with activated carbon as described immediately below prior to analysis.

A digested polyol sample is combined with activated carbon (100 mesh powder, 5 wt. %) and mixed thoroughly. The vessel is capped and placed in a 60° C. oven. Meanwhile, a filter bed is prepared using a Buchner funnel, filter paper, Celite® 545 filter aid, filter flask, and acetone. After pouring an acetone slurry of the filter aid and molding the surface to provide an even bed, the prepared funnel and a fresh filter flask are placed in the oven and allowed to warm to 60° C. over 10-30 min. Vacuum filtration is performed while keeping the funnel and polyol at or about 60° C. The warm polyol filtrate is subsequently re-filtered through a fresh Celite® 545 bed prepared and warmed as described previously to remove any remaining charcoal or other particulates.

Example 6

Preparation and Carbon Treatment of Dimer Fatty Acid-Modified Polyol from Recycled PET The procedure of Example 1 is generally followed to make a propylene glycol-digested rPET (3:1 moles PG/rPET). When the digestion is considered complete, the reaction mixture is cooled to 100° C. Pripol™ 1017 dimer fatty acid, product of Croda, is added (0.5 moles per mole of rPET), and the mixing rate is increased (200 rpm). When the addition is complete, a Dean-Stark trap is introduced between the reactor and condenser, and heating to 200° C. is resumed. Water generated in the condensation reaction is removed until roughly the theoretical amount is removed. When the reaction is complete, the polyol product is allowed to cool to 100° C. and is then decanted from the reactor and filtered through cheesecloth. A first portion of the product is not treated further. A second portion of the product is treated with activated carbon and filtered through Celite® 545 filter aid as described earlier. Results appear in Table 3.

Example 7

Preparation and Carbon Treatment of Dimer Fatty Acid-Modified Polyol from Recycled PET The procedure of Example 1 is generally followed to make a PG-digested rPET. The digested rPET is treated with activated carbon and filtered through Celite® 545 filter aid as described earlier. The treated polyol is then reacted with Pripol™ 1017 dimer fatty acid as described in Example 6. Results appear in Table 3.

Example 8

Preparation and Carbon Treatment of Tung Oil-Modified Polyol from Recycled PET The procedure of Example 6 is generally followed except that the propylene glycol-digested rPET (3:1 moles PG/rPET) is reacted with tung oil (1.3 moles per mole of rPET) instead of dimer fatty acid. Results appear in Table 3.

Comparative Example 9

Ethylene Glycol as the Glycol Reactant

A reactor equipped with an overhead mixer, condenser, heating mantle, thermocouple, and nitrogen inlet is charged with zinc acetate dihydrate (0.5 wt. %), green recycled polyethylene terephthalate pellets, and ethylene glycol (3.0 moles per mole of rPET). The mixture is heated for 3 h at 200° C. to accomplish digestion of the rPET flakes. Heating is discontinued, and the flask is cooled in an ambient air stream. The liquid begins to crystallize at 95° C., becomes opaque at 85° C., and is poured into a bottle. At room temperature, the product is a crystalline solid.

Analysis of Glycol-Digested rPET and Dimer Fatty Acid-Modified Products

Hydroxyl numbers and acid numbers are determined by standard methods (ASTM E-222 and ASTM D3399, respectively).

Viscosities are measured at 25° C. using a Brookfield DV-III Ultra rheometer with spindle #31 at 25%, 50%, and 75% torque.

Colorimetric Analysis

Results reported for CIE L*a*b* values are an average of transmission spectral properties obtained at an independent laboratory using two different spectrophotometers: a Cary® 100 Conc UV/vis spectrophotometer and an X-Rite color 8200 spectrophotometer (Varian). The Varian instrument is equipped with a 73-mm integrating sphere in the diffuse mode over a wavelength range of 360-830 nm. The X-Rite spectrophotometer is equipped with a 6-inch integrating sphere with a d/8° geometry over the 360-740 nm wavelength range in the spectrally included mode. All samples are analyzed at room temperature (except for Ex. 3, NPG-digested product, which is warmed to about 60° C., then cooled 5 min. prior to measurement) and evaluated versus water as the 100% calibration standard and reference. Samples and reference water are evaluated utilizing 10-mm path length disposable cuvettes. From the spectra obtained, D65/10 CIE L* a* b* values are calculated. Results appear in Tables 1 and 3.

Gel Permeation Chromatography Analysis

A Waters gel permeation chromatograph is used to analyze polyol samples diluted in tetrahydrofuran (12 mg polyol/4 mL THF). Pump: Waters 590; injector: Waters 717+ WISP; detector: Waters 486 UV at 295 nm; columns: Jordi 500 Å 250×10 mm catalog #15021; temperature: 37° C.; injection volume: 100 µL; flow rate: 1.0 mL/min.; sampling rate: 1.0 point per second; data processing: Millennium 2.10 software.

As is shown in Table 1, the polyester polyols have hydroxyl numbers below 800 mg KOH/g and desirably low viscosities at room temperature, which will facilitate their formulation into polyurethanes. Activated carbon treatment of the glycol-digested polyol increases the L* and a* values such that the color index, as defined herein, is less than 20 (preferably less than 15) following treatment. The color index is below 20 regardless of the choice of $C_3$-$C_{10}$ glycol reactant.

Table 2 shows the results of gel permeation chromatography analysis of glycol-digested rPET using ultraviolet detection. The relative amounts of BHAT (bis(hydroxyalkyl) terephthalate) and higher oligomers, including dimers (two terephthalate units) and trimers (three terephthalate units) are determined. As shown in the table, monomeric BHAT products predominate (53-60 wt. %), followed by dimers (28-30 wt. %) and trimers (9-12 wt. %) in this set of examples. The results are surprising in view of reports in the literature suggesting that dimers will predominate when similar reaction conditions are used to make propylene-glycol digested rPET.

Table 3 demonstrates that hydrophobe modification can be used before or after activated carbon treatment to give polyester polyols with low color index and workable polyol properties, including reasonably low room-temperature viscosities.

The preceding examples are mere illustrations; the following claims define the scope of the inventive subject matter.

TABLE 1

Effect of Activated Carbon Treatment on Polyol Properties: Effect of Glycol

| Ex | Treatment | L* | a* | b* | Color index | OH # mg KOH/g | Acid # mg KOH/g | Viscosity (cP at 25° C.) |
|---|---|---|---|---|---|---|---|---|
| | Digest green rPET with propylene glycol (3:1 PG to rPET) | | | | | | | |
| 1 | No filtration | 77.5 | −44.9 | 47.4 | 58 | 768 | 3.7 | 718 |
| | AC, filter 2× Celite | 94.9 | −10.7 | 27.3 | 11 | 762 | 6.1 | 482 |
| | Digest green rPET with propylene glycol (2.6:1 PG to rPET) | | | | | | | |
| 2 | No filtration | — | — | — | — | 734 | 6.3 | 847 |
| | AC, filter 2× Celite | — | — | — | — | 715 | 6.7 | 814 |
| | Digest green rPET with neopentyl glycol (3:1 NPG to rPET) | | | | | | | |
| 3 | No filtration | 17.2 | −18.7 | 17.0 | 109 | 628 | 1.3 | 1650 |
| | AC, filter 2× Celite | 52.4 | −5.1 | 43.7 | 10 | 634 | 1.7 | 1366 |
| | Digest green rPET with 2-methyl-1,3-propanediol (3:1 diol to rPET) | | | | | | | |
| 4 | No filtration | 68.6 | −31.2 | 41.5 | 45 | 720 | 2.4 | 882 |
| | AC, filter 2× Celite | 93.3 | −9.4 | 27.0 | 10 | 722 | 2.1 | 819 |
| | Digest green rPET with 3-methyl-1,5-pentanediol (3:1 diol to rPET) | | | | | | | |
| 5 | No filtration | 52.0 | −17.8 | 42.8 | 34 | 580 | 2.2 | 473 |
| | AC, filter 2× Celite | 94.7 | −12.9 | 36.2 | 14 | 652 | 2.8 | 443 |

DFA = dimer fatty acid;
AC = activated carbon treatment;
PG = propylene glycol;
rPET = recycled polyethylene terephthalate
Color index = 100 × (|a*|/L*)

TABLE 2

Summary of GPC Results

| | | Monomers (BHATs) | | Dimers | | Trimers | |
|---|---|---|---|---|---|---|---|
| Ex | Glycol | ret times | wt.% | ret times | wt.% | ret times | wt.% |
| 1 | propylene glycol (3:1) | 22.48 | 60.4 | 21.23 | 27.9 | 20.33 | 8.6 |
| 2 | propylene glycol (2.6:1) | 22.68, 22.52 | 58.0 | 21.27 | 28.9 | 20.37 | 9.6 |
| 4 | 2-methyl-1,3-propanediol (3:1) | 22.57, 21.67 | 56.5 | 20.77 | 29.1 | 19.82 | 10.2 |
| 5 | 3-methyl-1,5-pentanediol (3:1) | 22.30, 21.70 | 52.8 | 20.72, 20.37 | 29.6 | 19.45 | 11.8 |

Monomers (BHATs = bis(hydroxyalkyl)terephthalates) have one, dimers have two, and trimers have three terephthalate units.

TABLE 3

Effect of Hydrophobe Modification on Polyol Properties

| Ex | Treatment | L* | a* | b* | Color index | OH # mg KOH/g | Acid # mg KOH/g | Viscosity (cP at 25° C.) |
|---|---|---|---|---|---|---|---|---|
| | Digest green rPET with propylene glycol (3:1 PG to rPET); react with 0.5 moles of dimer fatty acid | | | | | | | |
| 6 | No filtration | 82.8 | −36.3 | 42.7 | 44 | 381 | 2.6 | 3091 |
| | AC, filter 2× Celite | 94.9 | −10.0 | 38.0 | 11 | 338 | 2.3 | 3658 |
| | Digest green rPET with propylene glycol (3:1 PG to rPET) | | | | | | | |
| 7 | AC, filter 2× Celite, react with DFA | 92.7 | −8.8 | 39.6 | 9.5 | 359 | 2.6 | 3339 |

TABLE 3-continued

Effect of Hydrophobe Modification on Polyol Properties

| Ex | Treatment | L* | a* | b* | Color index | OH # mg KOH/g | Acid # mg KOH/g | Viscosity (cP at 25° C.) |
|---|---|---|---|---|---|---|---|---|
| Digest green rPET with propylene glycol (3:1 PG to rPET); react with 1.3 moles of tung oil ||||||||| 
| 8 | No filtration | 83.2 | −22.7 | 57.6 | 27 | 414 | 1.5 | 555 |
|   | AC, filter 2× Celite | 90.4 | −5.8 | 47.3 | 6.4 | 388 | 1.7 | 529 |

DFA = dimer fatty acid;
AC = activated carbon treatment;
PG = propylene glycol;
rPET = recycled polyethylene terephthalate.
Color index = 100 × (|a*|/L*)

We claim:

1. A polyester polyol made by a process which comprises:
   (a) heating a composition comprising recycled polyethylene terephthalate (rPET) with a $C_3$-$C_{10}$ glycol reactant to give a digested intermediate comprising glycols and a terephthalate component, wherein the terephthalate component comprises, by gel permeation chromatography using ultraviolet detection, 45 to 70 wt. % of bis(hydroxyalkyl)terephthalates based on the amount of terephthalate component; and
   (b) treating the digested intermediate with activated carbon under conditions effective to give the polyester polyol;
   wherein the molar ratio of $C_3$-$C_{10}$ glycol reactant to rPET is at least 2.0:1, and the polyester polyol has a hydroxyl number within the range of 25 to 800 mg KOH/g and a color index less than 20, where color index is defined by 100×(|a*|/L*) as measured by CIE colorimetric analysis.

2. The polyol of claim 1 wherein the recycled polyethylene terephthalate comprises green rPET.

3. The polyol of claim 1 wherein the $C_3$-$C_{10}$ glycol reactant is selected from the group consisting of propylene glycol, diethylene glycol, triethylene glycol, dipropylene glycol, neopentyl glycol, 2-methyl-1,3-propanediol, 1,4-butanediol, 1,6-hexanediol, 3-methyl-1,5-pentanediol, and mixtures thereof.

4. The polyol of claim 1 wherein the terephthalate component further comprises 20 to 40 wt. % of terephthalate dimers based on the amount of terephthalate component.

5. The polyol of claim 1 wherein the terephthalate component comprises 45 to 65 wt. % of bis(hydroxyalkyl)terephthalates, 20 to 35 wt. % of terephthalate dimers, and 5 to 15 wt. % of terephthalate trimers, each based on the amount of terephthalate component.

6. The polyol of claim 1 wherein the terephthalate component comprises 50 to 60 wt. % of bis(hydroxyalkyl)terephthalates, 25 to 30 wt. % of terephthalate dimers, and 8 to 12 wt. % of terephthalate trimers, each based on the amount of terephthalate component.

7. A hydrophobe-modified polyester polyol of claim 1.

8. The polyol of claim 7 wherein the hydrophobe is a dimer fatty acid.

9. The polyol of claim 1 wherein the glycol reactant comprises propylene glycol.

10. The polyol of claim 1 wherein the glycol reactant comprises a recycled glycol.

11. The polyol of claim 1 having a hydroxyl number within the range of 40 to 500 mg KOH/g.

12. The polyol of claim 1 wherein the molar ratio of glycol reactant to rPET is within the range of 2.5:1 to 4.5:1.

13. The polyol of claim 1 having a viscosity at 25° C. less than 10,000 cP.

14. The polyol of claim 1 having a recycle content greater than 50 wt. %, wherein the recycle content is based on the combined amounts of rPET and any recycled $C_3$-$C_{10}$ glycol reactant.

15. The polyol of claim 1 wherein the rPET and glycol reactant are heated in the presence of a catalyst.

16. The polyol of claim 15 wherein the catalyst is zinc acetate or tetrabutyl titanate.

17. The polyol of claim 1 wherein the rPET and glycol reactant are heated at a temperature within the range of 80° C. to 260° C.

18. The polyol of claim 1 having a color index less than 15.

19. A polyurethane, polyisocyanurate, or prepolymer made from the polyester polyol of claim 1.

20. A process which comprises:
   (a) heating a composition comprising recycled polyethylene terephthalate (rPET) with a $C_3$-$C_{10}$ glycol reactant to give a digested intermediate comprising glycols and a terephthalate component, wherein the terephthalate component comprises, by gel permeation chromatography using ultraviolet detection, 45 to 70 wt. % of bis(hydroxyalkyl)terephthalates based on the amount of terephthalate component; and
   (b) treating the digested intermediate with activated carbon under conditions effective to give a polyester polyol;
   wherein the molar ratio of $C_3$-$C_{10}$ glycol reactant to rPET is at least 2.0:1, and the polyester polyol has a hydroxyl number within the range of 25 to 800 mg KOH/g and a color index less than 20, where color index is defined by 100×(|a*|/L*) as measured by CIE colorimetric analysis.

21. The process of claim 20 wherein the recycled polyethylene terephthalate comprises green rPET.

* * * * *